United States Patent
Pouillot et al.

(10) Patent No.: US 10,260,051 B2
(45) Date of Patent: Apr. 16, 2019

(54) **PHAGE THERAPY OF *PSEUDOMONAS* INFECTIONS**

(71) Applicant: PHERECYDES PHARMA, Romainville (FR)

(72) Inventors: Flavie Pouillot, Paris (FR); Helene Blois, Paris (FR)

(73) Assignee: PHERECYDES PHARMA, Romainville (FR)

(*) Notice: Subject to any disclaimer, the term of this patent is extended or adjusted under 35 U.S.C. 154(b) by 0 days.

(21) Appl. No.: 16/131,075

(22) Filed: Sep. 14, 2018

(65) Prior Publication Data

US 2019/0002840 A1    Jan. 3, 2019

Related U.S. Application Data

(63) Continuation of application No. 15/031,763, filed as application No. PCT/EP2014/072905 on Oct. 24, 2014, now Pat. No. 10,077,431.

(30) Foreign Application Priority Data

Oct. 25, 2013  (EP) ..................... 13306471

(51) Int. Cl.
| | |
|---|---|
| *A61K 39/00* | (2006.01) |
| *A61K 39/395* | (2006.01) |
| *C07K 16/28* | (2006.01) |
| *A61K 45/06* | (2006.01) |
| *C07K 16/00* | (2006.01) |
| *C12N 7/00* | (2006.01) |
| *C12Q 1/18* | (2006.01) |
| *C07K 14/005* | (2006.01) |
| *A61K 35/76* | (2015.01) |

(52) U.S. Cl.
CPC .............. *C12N 7/00* (2013.01); *A61K 35/76* (2013.01); *C07K 14/005* (2013.01); *C12Q 1/18* (2013.01); *C12N 2795/10121* (2013.01); *C12N 2795/10122* (2013.01); *C12N 2795/10132* (2013.01); *C12N 2795/10171* (2013.01); *C12N 2795/10221* (2013.01); *C12N 2795/10222* (2013.01); *C12N 2795/10232* (2013.01); *C12N 2795/10271* (2013.01)

(58) Field of Classification Search
CPC ........ A61K 2039/505; C07K 2317/565; C07K 2317/92; C07K 2317/76; C07K 2317/21
See application file for complete search history.

(56) References Cited

FOREIGN PATENT DOCUMENTS

EP    2465926    6/2012

OTHER PUBLICATIONS

Alemayehu, D. et al. "Bacteriophages φMR299-2 and φNH-4 Can Eliminate *Pseudomonas aeruginosa* in the Murine Lung and on Cystic Fibrosis Lung Airway Cells" *MBIO*, Mar. 6, 2012, pp. 1-9, vol. 3, No. 2, Article No. e0002912.

Ceyssens, P.-J. et al. "Comparative analysis of the widespread and conserved PB1-like viruses infecting *Pseudomonas aeruginosa*" *Environmental Microbiology*, 2009, pp. 2874-2883, vol. 11, No. 11.

Fu, W. et al. "Bacteriophage Cocktail for the Prevention of Biofilm Formation by *Pseudomonas aeruginosa* on Catheters in an In Vitro Model System" *Antimicrobial Agents and Chemotherapy*, Jan. 1, 2010, pp. 397-404, vol. 54, No. 1.

Fukuda, K. et al. "*Pseudomonas aeruginosa* Keratitis in Mice: Effects of Topical Bacteriophage KPP12 Administration" *PLOS ONE*, Oct. 2012, pp. 1-8, vol. 7, No. 10, Article No. e47742.

Garbe, J. et al. "Characterization of JG024, a pseudomonas aeruginosa PB1-like broad host range phage under simulated infection conditions" *BMC Microbiology*, Nov. 26, 2010, pp. 1-10, vol. 10, No. 1.

Krylov, V. et al. "A Genetic Approach to the Development of New Therapeutic Phages to Fight *Pseudomonas aeruginosa* in Wound Infections" *Viruses*, Dec. 21, 2012, pp. 15-53, vol. 5.

McVay, C.S. et al. "Phage Therapy of *Pseudomonas aeruginosa* Infection in a Mouse Burn Wound Model" *Antimicrobial Agents and Chemotherapy*, Jun. 2007, pp. 1934-1938, vol. 51, No. 6.

Oikonomou, O. et al. "Investigation of carbapenem heteroresistance among different sequence types of *Pseudomonas aeruginosa* clinical isolates reveals further diversity" *J. Med. Microbiology*, May 19, 2011, pp. 1556-1558, vol. 60, No. 10.

Wright, A. et al. "A controlled clinical trial of a therapeutic bacteriophage preparation in chronic otitis due to antibiotic-resistant *Pseudomonas aeruginosa*; a preliminary report of efficacy" *Clin. Otolaryngol.* 2009, pp. 349-357, vol. 34.

Database EMBL [Online] Accession No. FM887021, "Comparative analysis of the widespread and conserved PB1-like viruses infecting Pseudomonas aeruginosa" Dec. 16, 2008, pp. 1-36, XP-002718979.

Database EMBL [Online] Accession No. AM910650, "Analysis of the genome, proteome and transcriptome of Pseudomonas aeruginosa phage LUZ24" Nov. 27, 2007, pp. 1-26, XP-002718980.

Database EMBL [Online] Accession No. JN254801, "Bacteriophages PhiMR299-2 and PhiNH-4 Can Eliminate Pseudomonas aeruginosa in the Murine Lung and on Cystic Fibrosis Lung Airway Cells" Apr. 27, 2012, pp. 1-32, XP-055161973.

Database EMBL [Online] Accession No. EU716414, "Comparative analysis of the widespread and conserved PB1-like viruses infecting Pseudomonas aeruginosa" Jan. 6, 2009, pp. 1-39, XP-002718981.

Database EMBL [Online] Accession No. JN254800, "Bacteriophages PhiMR299-2 and PhiNH-4 Can Eliminate Pseudomonas aeruginosa in the Murine Lung and on Cystic Fibrosis Lung Airway Cells" Mar. 13, 2012, pp. 1-41, XP-002718982.

Database EMBL [Online] Accession No. GU815091, "Characterization of JG024, a pseudomonas aeruginosa PB1-like broad host range phage under simulated infection conditions" Dec. 16, 2010, pp. 1-64, XP-055162017.

Database EMBL [Online] Accession No. KC294142, "Pseudomonas aeruginosa phage PaP4" Jan. 16, 2013, pp. 1-29, XP-002718983.

(Continued)

*Primary Examiner* — Barry A Chestnut
(74) *Attorney, Agent, or Firm* — Saliwanchik, Lloyd & Eisenschenk

(57) ABSTRACT

The present invention relates to bacteriophage therapy. More particularly, the present invention relates to novel bacteriophages having a high specificity against *Pseudomonas aeruginosa* strains, their manufacture, components thereof, compositions comprising the same and the uses thereof in phage therapy.

10 Claims, 2 Drawing Sheets

Specification includes a Sequence Listing.

(56) References Cited

OTHER PUBLICATIONS

Database EMBL [Online] Accession No. AB560486, "Pseudomonas aeruginosa Keratitis in Mice: Effects of Topical Bacteriophage KPP12 Administration" Aug. 23, 2012, pp. 1-35, XP-002718984.
Database EMBL [Online] Accession No. FM201282, "Genome and proteome analysis of newly isolated Pseudomonas aeruginosa phages" Aug. 22, 2008, pp. 1-37, XP-002718985.
Written Opinion in International Application No. PCT/EP2014/072905, dated Jan. 27, 2015, pp. 1-11.
Database EMBL, 2008, Pseudomonas phage SN, complete genome: accession No. FM887021: pdf pp. 1-32.
Alemayehu, D. et al. "Bacteriophages ØMR299-2 and ØNH-4 Can Eliminate *Pseudomonas aeruginosa* in the Murine Lung and on Cystic Fibrosis Lung Airway Cells" *MBio*. Mar./Apr. 2012, pp. 1-9, vol. 3, No. 2.
Wang, I.-N., et al. "HOLINS: The Protein Clocks of Bacteriophage Infections" *Annu. Rev. Microbiol.* 2000, pp. 1-34, vol. 54.

PHAGE THERAPY OF *PSEUDOMONAS* INFECTIONS

CROSS-REFERENCE TO RELATED APPLICATIONS

This application is a continuation of U.S. application Ser. No. 15/031,763, filed Apr. 25, 2016, now U.S. Pat. No. 10,077,431, which is the U.S. national stage application of International Patent Application No. PCT/EP2014/072905, filed Oct. 24, 2014.

The Sequence Listing for this application is labeled "Seq-List.txt" which was created on Apr. 8, 2016 and is 934 KB. The entire content of the sequence listing is incorporated herein by reference in its entirety.

The present invention relates to novel bacteriophages, compositions comprising the same, their manufacture, and the uses thereof. The invention is particularly adapted for the treatment of an infection in a mammal and for improving a subject condition by modifying the flora in said subject.

BACKGROUND OF THE INVENTION

Bacteriophages (or phages) are small viruses displaying the ability to infect and kill bacteria while they do not affect cells from other organisms. Initially described almost a century ago by William Twort, and independently discovered shortly thereafter by Félix d'Herelle, more than 6000 different bacteriophages have been discovered so far and described morphologically, including bacterial and archaeal viruses. The vast majority of these viruses are tailed while a small proportion are polyhedral, filamentous or pleomorphic. They may be classified according to their morphology, their genetic content (DNA vs. RNA), their specific host, the place where they live (marine virus vs. other habitats), and their life cycle. As intra-cellular parasites of bacterial cells, phages display different life cycles within the bacterial host: lytic, lysogenic, pseudo-lysogenic, and chronic infection (Weinbauer, 2004; Drulis-Kawa, 2012). Lytic phages cause lysis of the host bacterial cell as a normal part of their life cycle. Lysogenic phages (also termed temperate phages) can either replicate by means of the lytic life cycle and cause lysis of the host bacterium, or they can incorporate their DNA into the host bacterial DNA and become noninfectious prophages. Whatever the type of cycle of a phage life, the first step is the attachment to receptors of the bacterial cell wall before phage material may enter the bacteria. This specific process influences the spectrum of the possible phage-bacteria interactions.

Bacteriophages are commonly used as research tools to modify bacteria in laboratory experiments.

Because of their target host cell specificity, the use of phages as a therapy to treat acute and chronic infections has been considered, particularly in dermatology, ophthalmology, urology, stomatology, pediatrics, otolaryngology or surgery. This concept of therapeutic use of phages to treat bacterial infection was, however, highly controversial from the very beginning and not widely accepted by the public or medical community. Early studies were widely criticized for lack of appropriate controls and inconsistent results. The lack of reproducibility and many conflicting results obtained in the various published studies led the Council on Pharmacy and Chemistry of the American Medical Association to conclude that the evidence for the therapeutic value of lytic filtrates was for the most part contradictory and unconvincing, and recommend additional research to confirm its purported benefits.

Since the introduction of antibiotics in the 1940s, little attention was paid to this field of therapeutics, especially in the Western world. But the extensive use of antibiotics has led to the widespread emergence and spread of antibiotic-resistant bacteria around the world, causing increasingly serious problems. It has therefore become a major therapeutic challenge to overcome the limited therapeutic options remaining to treat major multi-drug resistant microbes.

In addition, many pathogenic microorganisms reside within biofilms, which biofilms cause additional problems when designing new anti-microbial agents. In this regard, bacteria growing as a biofilm rather than in single-celled ("planktonic") forms tend to be particularly resistant to anti-microbial agents and to be particularly difficult for the host immune system to render an appropriate response.

Since its initial discovery in the late 19th century (Fordos 1859), the Gram-negative bacterium *Pseudomonas aeruginosa* has gained a notorious place in the list of infamous human pathogens (Williams et al., 1894; Freeman et al., 1916). The arrival of the antibiotic era largely palliated the previously fatal outcome of acute infections in healthy patients. Only a relative improvement has been achieved in the eradication of chronic infections, which develop mainly in individuals suffering from cystic fibrosis or severe burns or who are immunocompromised (Gang et al., 1999; Jones et al., 2010). Two intrinsically related factors in the fatal outcome of infection in these patients are the rapid prescription of inappropriate antibiotic treatments and the development or acquisition of multidrug-resistant strains. While the use of (an) appropriate antibiotic(s) has been reported as an essential factor in the eradication of *P. aeruginosa* infections (Kang et al., 2005; Micek et al., 2005), conversely, antibiotic abuse significantly contributes to increasing resistance by exerting a continuous selective pressure for the acquisition of such capabilities. Antibiotics alone do not account for the high prevalence of multidrug-resistant variants: *P. aeruginosa* has multiple, chromosomally encoded intrinsic mechanisms of resistance, including low permeability of the cell envelope and numerous multidrug efflux pumps. Another major factor accounting for the successful invasive behavior and persistence of this bacterium is its high adaptability, allowing rapid colonization of different environments.

Furthermore, pathogenic bacteria such as *P. aeruginosa* are able to form biofilms, which contribute to their increased resistance to antibiotics. Such biofilms may comprise more than one type of bacteria supported and surrounded by an excreted extracellular matrix, and assist bacteria to colonize various surfaces. Biofilms allow bacteria to attach to surfaces and to reach population densities which would otherwise be unsupportable, imparting increased resistance to not only antibiotics but many environmental stresses including toxins such as heavy metals, bleaches and other cleaning agents. It is known that bacteria within biofilms can be 100 to 1000 times more resistant to antibiotics than the same strain of bacteria growing in planktonic forms. Such an increased resistance means that bacteria that are apparently sensitive to antibiotics in a laboratory test may be resistant to therapy in a clinical setting. Even if some are cleared, biofilms may provide resistant reservoirs permitting rapid colonization once antibiotics are no longer present. It is therefore obvious that biofilms are major factors in many human diseases. Chemical treatments are unsuited for use against biofilms since this is precisely what they have evolved to counter. Physical abrasion does provide a means to disrupt biofilms. Unfortunately, many surfaces where biofilms support bacterial pathogenesis are poorly suited to rigorous abrasion, i.e., bones, joints, implanted medical devices, etc. For example, the surfaces of wounds or burns are extremely sensitive and delicate. Even where abrasion is both suitable and in routine use, clearing of biofilms is limited. Oral plaque on the surface of teeth is a biofilm and is partially cleared by regular brushing. However, bacteria are maintained on unbrushed surfaces (for example in the gaps between teeth) and can recolonize cleared surfaces both rapidly and effectively. From this, it is clear that existing approaches to clearing biofilms are of limited efficacy.

The capability for quick adaptation and the ability to form biofilms are the main reasons that identify P. aeruginosa as opportunistic pathogens. They have acquired the status of hospital pathogens, and may be isolated from clinical samples taken from wounds, sputum, bladder, urethra, vagina, ears, eyes and respiratory tract. The emergence of resistance to the most powerful new antibiotics in such clinical P. aeruginosa strains, occurring even during treatment, makes the fight with P. aeruginosa hospital pathogens a great problem.

Furthermore, it has been reported that the pathological or physiological condition of a subject is influenced by the balance of microorganisms in the flora of the subject. Accordingly, modifying the microbial flora, or modifying said balance, or restoring said balance, by destroying P. aeruginosa population, is also a valuable approach for improving a subject condition.

Therefore, there is a great need for new antibacterial agents or compositions that can be used to destroy P. aeruginosa strains, even when organized in bacterial biofilms, suitable for use in human or animal therapy, as well, as for decontaminating materials.

SUMMARY OF THE INVENTION

The inventors have isolated and characterized new bacteriophages presenting specific lytic activity to Pseudomonas aeruginosa (P. aeruginosa), which can be used as active agents in pharmaceutical or veterinary preparations, particularly to treat P. aeruginosa bacterial infections or to modify microbial balance in a subject. The new bacteriophages of the invention exhibit strong lytic activity and high selectivity, and can be combined to induce controlled destruction of a very large spectrum of P. aeruginosa cells.

An object of the invention is to provide antibacterial compositions comprising at least one, preferably at least two bacteriophages having lytic activity against a Pseudomonas aeruginosa (P. aeruginosa) strain, said bacteriophages being selected from the bacteriophages having a genome comprising a nucleotide sequence of any one of SEQ ID NOs: 1 to 13 or a sequence having at least 90% identity thereto.

A further object of the invention relates to a bacteriophage having lytic activity to a Pseudomonas aeruginosa (P. aeruginosa) strain and having a genome comprising a nucleotide sequence selected from any one of SEQ ID NOs: 1 to 13 or a sequence having at least 97% identity thereto.

The bacteriophages of the invention exhibit lytic activity to multi drug resistant strains of P. aeruginosa, in particular to antibiotic resistant pathogenic strains, such as cephalosporinase, carbenicillinases and extended-spectrum β-lactamases (Strateva T. and Yordanov D. 2009).

In another aspect, the invention is related to a bacteriophage having lytic activity to a pathogenic P. aeruginosa strain, wherein the bacteriophage is specific for P. aeruginosa, active against antibiotic-resistant P. aeruginosa strains, and has a productive lytic effect below 20.

The invention further concerns an isolated nucleic acid contained in a bacteriophage of the invention, preferably an isolated nucleic acid molecule comprising a nucleotide sequence selected from any one of SEQ ID NOs: 1 to 13 or a sequence having at least 97% identity thereto, as well as an isolated polypeptide encoded by said nucleic acid.

Another object of the invention is a composition comprising a nucleic acid or polypeptide as defined above.

The compositions of the invention typically further comprise a pharmaceutically or veterinary acceptable excipient or carrier. They may be liquid, semi-liquid, solid or lyophilized.

Another object of the invention relates to a bacteriophage, nucleic acid, polypeptide or composition as defined above, for use in the treatment of an infection in a mammal, for modifying the microbial flora in a mammal, for decontaminating a material and/or for killing a P. aeruginosa bacterium or for compromising the integrity of a bacterial biofilm.

The invention relates also to the use of one or several lytic bacteriophages to improve a subject condition by modifying the microbial flora in said subject. The microbial flora may be modified by correcting, adapting or restoring a proper balance of microorganisms in said flora.

The invention also relates to a method for treating an infection in a mammal, comprising the administration to said mammal of at least one bacteriophage, nucleic acid, polypeptide or composition as defined above.

The invention also relates to a method for treating a surface or material suspected of being contaminated with a P. aeruginosa bacterium, comprising applying to said surface or material at least one bacteriophage, nucleic acid, polypeptide or composition as defined above. The surface or material may be a surface of any device, vessel or laboratory material, cloth, etc.

A further object of the invention relates to a kit comprising a composition as defined above and a means for applying the same to a subject or surface.

Another object of the invention relates to a method for predicting or determining efficacy of a bacteriophage therapy in a subject, wherein the method comprises determining in vitro a lytic activity of one or more bacteriophages of the invention to a P. aeruginosa strain from a sample of said subject, a lytic activity of one or more bacteriophages of the invention to at least one P. aeruginosa strain from said sample being indicative of an efficient treatment. The method further optionally comprises the step of treating the subject with at least one bacteriophage having a lytic activity to a P. aeruginosa strain from a sample of said subject.

In another aspect, the invention provides a method for selecting a subject or determining whether a subject is susceptible to benefit from a bacteriophage therapy, wherein the method comprises the step of determining in vitro a lytic activity of one or more bacteriophages of the invention to a P. aeruginosa strain from a sample of said subject, a lytic activity of one or more of said bacteriophages to at least one P. aeruginosa strain being indicative of a responder subject.

The invention may be used in any mammal, preferably in human beings, or to treat any material, including laboratory materials or medical devices.

DETAILED DESCRIPTION OF THE INVENTION

Figure 1:
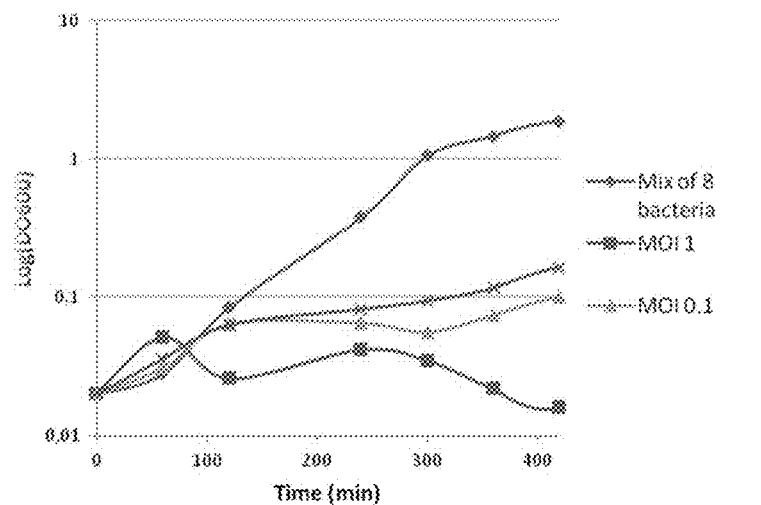
FIG. 1: In vitro efficacy of Bacteriophages of the invention on various combinations of P. aeruginosa strains.

The present invention relates to novel bacteriophages, components thereof, compositions comprising the same, their manufacture, and the uses thereof as antibacterial agents, particularly for the treatment of an infection in a mammal and for improving a subject condition by modifying the microbial flora in said subject.

Definitions

To facilitate understanding of the invention, a number of terms are defined below.

As used herein, the term "bacteriophage" or "phage" refers to a functional phage particle comprising a nucleic acid genome packaged in a proteinaceous envelope or capsid. The term also refers to portions of the bacteriophage, including, e.g., a head portion, or an assembly of phage components, which provide substantially the same functional activity.

The term "phenotypic characteristic" designates more preferably the morphology and/or host-range of a bacteriophage. Methods for phenotyping bacteriophages are well known per se in the art and include, for example, determining bacterial host range and/or activity against the biofilm produced by certain bacterial strains.

The term "lytic activity" as used in the invention designates the property of a bacteriophage to cause lysis of a bacterial cell. The lytic activity of a bacteriophage can be tested on *P. aeruginosa* strains according to techniques known per se in the art (see also Examples section).

The term "variant" of a reference bacteriophage designates bacteriophages having variation(s) in the genomic sequence and/or polypeptide(s) encoded thereby as compared to said reference bacteriophage, while retaining the same phenotypic characteristics as the reference bacteriophage. Variants typically comprise, e.g., silent mutations, conservative mutations, minor deletions, and/or minor replications of genetic material, and retains phenotypic characteristics of the reference bacteriophage. In a preferred embodiment, the variant of the invention retain any observable characteristic or property that is dependent upon the genome of the bacteriophage of the invention, i.e. phenotypic characteristics of said bacteriophage and/or lytic activity against the *P. aeruginosa* strains. Preferred variants have less than 5% nucleic acid variation as compared to the genome of the reference bacteriophage, even more preferably less than 4%, more preferably less than 2%. Alternatively, or in combination, variants have preferably less than 5% amino acid variation in a coded polypeptide sequence as compared to a polypeptide of the reference bacteriophage.

The term "% identity" in relation to nucleic acid or amino acid sequences designates the level of identity or homology between said sequences and may be determined by techniques known per se in the art. Typically, the % identity between two nucleic acid or amino acid sequences is determined by means of computer programs such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C. D., 1970, Journal of Molecular Biology, 48, 443-453). With settings adjusted to e.g., DNA sequences (particularly, GAP creation penalty of 5.0 and GAP extension penalty of 0.3), nucleic acid molecules may be aligned to each other using the Pileup alignment software available as part of the GCG program package. The % identity between two sequences designates the identity over the entire length of said sequences.

The term "fragment" of a nucleic acid designates typically a fragment having at least 10 consecutive nucleotides of said nucleic acid, more preferably at least 15, 20, 25, 30, 35, 40, 50 or more consecutive nucleotides of said nucleic acid.

The term "fragment" of a polypeptide designates typically a fragment having at least 5 consecutive amino acids of said polypeptide, more preferably at least 10, 15, 20, 30, 40, 50 or more consecutive amino acids of said polypeptide.

The terms "ESBL *P. aeruginosa* strain" refers to cephalosporinase and/or extended-spectrum β-lactamases producing *P. aeruginosa* strains, including various forms of antibiotic resistance such as AmpC β-lactamase or Class A carbenicillin hydrolyzing β-lactamases, etc.

The term "specific" or "specificity" in relation to a bacteriophage refers to the type of host that said bacteriophage is able to infect. Specificity is usually mediated by the tail fibers of bacteriophages, which are involved in the interaction with receptors expressed on cells. A bacteriophage "specific" for *P. aeruginosa* more preferably designates a bacteriophage which can infect one or several *P. aeruginosa* strains and which cannot infect non-*P. aeruginosa* bacteria under physiological conditions.

As used herein, the term "polypeptide" refers to polypeptides of any size, including small peptides of e.g., from 5 to 20 amino acids, longer polypeptides, proteins or fragments thereof.

The term "PLE" or "Productive Lytic Effect" designates the ratio between burst size and productive lytic time of a given bacteriophage. Burst size and productive lytic time are parameters defining phage-host interaction and correspond, respectively, to the mean yield of bacteriophage particles produced by infection of one bacterium by one phage, and to the time taken by a free bacteriophage to lyse a bacterial cell.

In the context of the present specification, the term "isolated bacteriophage" should be considered to mean material removed from its original environment in which it naturally occurs. In relation to a bacteriophage, the term designates, particularly, a phage that is e.g., cultivated, purified and/or cultured separately from the environment in which it is naturally located. In relation to a nucleic acid or polypeptide, the term "isolated" designates e.g., a nucleic acid molecule or polypeptide which is separated from at least some of the components of its natural environment such as, e.g., a protein, lipid, and/or nucleic acid.

The term "pharmaceutically or veterinary acceptable" as used herein refers to any material (e.g., carrier, excipient or vehicle) that is compatible for use in a mammalian subject. Such includes physiologically acceptable solutions or vehicles that are harmless or do not cause any significant specific or non-specific immune reaction to an organism or do not abrogate the biological activity of the active compound. For formulation of the composition into a liquid preparation, saline, sterile water, Ringer's solution, buffered physiological saline, albumin infusion solution, dextrose solution, maltodextrin solution, glycerol, ethanol, and mixtures thereof may be used as a pharmaceutically or veterinary acceptable excipient or carrier. If necessary, other conventional additives such as thickeners, diluents, buffers, preservatives, surface active agents, antioxidants and bacteriostatic agents may be added. Further, diluents, dispersants, surfactants, binders and lubricants may be additionally added to the composition to prepare injectable formulations such as aqueous solutions, suspensions, and emulsions, oral formulations such as pills, capsules, granules, or tablets, or powdered formulations.

As used herein, "PFU" means plaque forming unit, as it is well defined in the art. Lytic bacteriophages lyse the host cell, causing a zone of clearing (or plaque) on a culture plate. Theoretically, each plaque is formed by one phage and the number of plaques multiplied by the dilution factor is equal to the total number of phages in a test preparation.

The term "treatment" or "therapy" designates a curative or a prophylactic treatment of a disease. A curative treatment is defined as a treatment that results in a cure of a disease, or a treatment that alleviates, reduces, stabilizes, or eliminates the symptoms of a disease or the suffering that it causes, directly or indirectly, or that improves a subject condition or reduces progression of a disease. A prophylactic treatment comprises both a treatment resulting in the prevention of a disease and a treatment reducing and/or delaying the incidence of a disease or the risk of its occurrence.

The term "mammal" includes human subjects as well as non-human mammals such as pets (e.g., dogs, cats), horses, ruminants, sheep, goats, pigs, etc.

The term "biofilm" as used herein designates a heterogeneous bacterial formation growing on various surfaces; preferably a bacterial community growing embedded in an exopolysaccharide matrix adhered onto solid biological or non-biological surfaces.

The term "compromise" as used herein refers to any alteration of the integrity. By compromising a bacterial biofilm, it is understood a penetration of the biofilm by bacteriophage, an infection of biofilm-associated bacteria and/or a lysis thereof and/or a partial or an entire clearing of the biofilm (i.e., by stopping colonization and/or disrupting biofilms).

The term "sample", as used herein, means any sample containing cells. Examples of such samples include fluids such as blood, plasma, saliva, or urine as well as biopsies, organs, tissues or cell samples. The sample may be treated prior to its use.

As used herein, the term "subject" or "patient" refers to an animal, preferably to a mammal, even more preferably to a human, including adult and child. However, the term "subject" also encompasses non-human animals, in particular mammals such as dogs, cats, horses, cows, pigs, sheep and non-human primates, among others.

The term "efficacy" of treatment or "response" to a bacteriophage therapy as used herein refers to a treatment which results in a decrease in the number of *P. aeruginosa* strains in a subject after bacteriophage treatment when compared to the number of *P. aeruginosa* strains before treatment. A "good responder" subject refers to a subject who shows or will show a clinically significant recovery when treated with a bacteriophage therapy.

The term "Cocktail" or composition of bacteriophages designates a combination of different types of bacteriophages. The bacteriophages in a cocktail/composition are preferably formulated together, i.e., in a same vessel or packaging, although they may be used as kits of parts wherein the (or some of the) bacteriophages are formulated or packaged separately and combined when used or administered.

DESCRIPTION OF EMBODIMENTS

The present invention is related to novel bacteriophage therapies. More particularly, the present invention relates to novel bacteriophages having a high specificity against *Pseudomonas aeruginosa* strains, their manufacture, components thereof, compositions comprising the same and the uses thereof in phage therapy.

Bacteriophages:

In a first aspect, the invention discloses the isolation and characterization of novel bacteriophages that are specific for *P. aeruginosa* strains and present, either alone or in combination(s), remarkable host range spectrum of lytic activity. These bacteriophages have been selected from environmental samples, isolated, sequenced, and characterized. As indicated, the bacteriophages are, individually and in combination(s), active against *P. aeruginosa* strains. They are remarkably effective against pathogenic *P. aeruginosa* strains, such as antibiotic-resistant *P. aeruginosa* strains, such as an ESBL *P. aeruginosa* strain. Furthermore, bacteriophages of the invention have a remarkably productive lytic effect ("PLE") below 20, more preferably below 15 and still more preferably between 0.3 and 15. Moreover, the bacteriophages of the invention are specific for *P. aeruginosa* strains, i.e., they do not cause lysis of non-*P. aeruginosa* bacteria. As will be illustrated further, the invention shows that these bacteriophages can be combined and formulated in conditions suitable for use as pharmaceutical or veterinary agents to exhibit targeted and very potent antibacterial effect against a controlled spectrum of *P. aeruginosa* strains.

More specifically, the following bacteriophages have been selected and characterized. Their corresponding nucleic acid sequences are also indicated.

TABLE 1

| SEQ ID number | Bacteriophage |
| --- | --- |
| SEQ ID NO: 1 | BP1384 |
| SEQ ID NO: 2 | BP1429 |
| SEQ ID NO: 3 | BP1430 |
| SEQ ID NO: 4 | BP1433 |
| SEQ ID NO: 5 | BP1450 |
| SEQ ID NO: 6 | BP1644 |
| SEQ ID NO: 7 | BP1647 |
| SEQ ID NO: 8 | BP1648 |
| SEQ ID NO: 9 | BP1649 |
| SEQ ID NO: 10 | BP1650 |
| SEQ ID NO: 11 | BP1658 |
| SEQ ID NO: 12 | BP1661 |
| SEQ ID NO: 13 | BP1662 |

The lytic profile of these bacteriophages has been determined on a broad number of *P. aeruginosa* strains. These bacteriophages have been selected for their potency and combination potential, as disclosed in the following table. In this table, the lytic effect of the bacteriophages on reference and pathogen-resistant strains are presented, to confirm the high lytic potential.

TABLE 2

| Bacteria | Phage | | | | | | | | | | | | |
|---|---|---|---|---|---|---|---|---|---|---|---|---|---|
| | 1384 | 1429 | 1430 | 1433 | 1450 | 1644 | 1647 | 1648 | 1649 | 1650 | 1658 | 1661 | 1662 |
| LMG 24882 | + | + | + | + | + | + | + | + | + | + | + | + | |
| LMG 24883 | + | +/− | + | + | + | + | + | + | + | | | + | + |
| LMG 24886 | + | | | + | + | + | +/− | | + | | +/− | + | |
| LMG 24887 | +/− | +/− | +/− | + | + | +/− | | | + | | + | +/− | +/− |
| LMG 24891 | + | + | + | + | + | + | + | + | + | | + | + | + |
| LMG 24892 | + | + | + | + | + | + | + | | + | | +/− | + | + |
| LMG 24893 | + | + | + | + | + | + | + | + | + | + | + | + | + |
| LMG 24896 | + | + | + | + | + | + | + | + | + | + | + | + | + |
| LMG 24898 | + | + | + | + | + | + | + | + | + | + | + | + | + |
| LMG 24901 | | +/− | + | | | | +/− | | | | | | |
| LMG 24903 | | | +/− | +/− | + | | + | | | | | | +/− |
| LMG 24904 | | +/− | +/− | +/− | + | | | | | | | | +/− |
| LMG 24905 | +/− | | | + | + | + | | | + | + | | | |
| LMG 24909 | + | +/− | | + | + | + | | + | + | + | +/− | + | |
| LMG 24913 | | | | +/− | + | | | | | + | +/− | +/− | |
| LMG 24916 | | + | + | + | | | + | | | | | | + |

Further results on highly resistant strains from wound or burn are presented below, further confirming the remarkable activity profile of the bacteriophages of the invention, and their complementarity.

TABLE 3

| | 1384 | 1429 | 1430 | 1433 | 1450 | 1644 | 1647 | 1648 | 1649 | 1650 | 1658 | 1661 | 1662 | CAR* |
|---|---|---|---|---|---|---|---|---|---|---|---|---|---|---|
| LMG 25000 | + | + | + | − | + | + | + | − | + | − | + | + | − | 1 |
| LMG 25122 | − | − | − | − | + | + | − | − | + | − | + | + | − | 5 |
| LMG 25140 | − | + | − | − | + | + | − | − | + | − | + | + | + | 5 |
| LMG 25133 | − | − | − | + | + | − | + | − | − | − | + | + | − | 2 |
| LMG 25165 | − | − | + | − | − | − | + | − | − | − | − | + | − | 5 |
| LMG 25146 | − | − | − | − | + | + | − | − | + | − | + | + | − | 4 |

*CAR: Class ATB Resistance

As can be seen from Tables 2 and 3, the phages have individually very strong lytic power, and combinations (or cocktails) of these bacteriophages may be produced that are able to kill all of the tested *P. aeruginosa* strains, thereby producing broad spectrum antibacterial compositions.

As an illustration, a cocktail of all 13 phages of the invention is able to effectively kill all bacteria listed in Table 2 and Table 3.

Moreover, the specificity of the bacteriophages has been tested on many non-*P. aeruginosa* strains. More particularly, the Examples section demonstrates that the bacteriophages of the invention have no lytic effect on any bacteria selected from *Escherichia coli*, *Acinetobacter baumannii*, *Enterobacter aerogenes*, *Enterobacter asburiae*, *Enterobacter cloacae*, *Klebsiella pneumonia*, *Porteus mirabilis*, *Staphylococcus aureus*, *Stenotrophomonas maltophilia* and/or *Serratia marcescens*.

A particular object of the invention thus resides in a bacteriophage having lytic activity to a *P. aeruginosa* strain and having a genome comprising a nucleotide sequence selected from any one of SEQ ID NOs: 1 to 13 or a sequence having at least 97% identity thereto, preferably at least 98% or 99% identity thereto.

The bacteriophages of the invention may be cultured, expanded, isolated, purified, and used in e.g., phage therapy of *P. aeruginosa*-mediated disorders, as will be disclosed in more detail below. Furthermore, variants of these bacteriophages retaining a phenotypic (e.g., specificity and lytic activity) of the bacteriophages can be produced and/or isolated by techniques known per se in the art.

The bacteriophages of the invention can be prepared by standard culture, isolation and purification methods. For example, *P. aeruginosa* producing bacteria are cultured, infected by a sample of a bacteriophage, and then treated to remove bacterial cells and debris. The enriched bacteriophage solution can be plated in a medium, for example agar medium, with embedded susceptible host strains of *P. aeruginosa* to obtain plaques. Then, single plaque can be picked out for subsequent bacteriophage purification and amplification. One or more cycles of selective amplification of bacteriophages of the invention may be performed, for example by mixing bacteriophages with the competent *P. aeruginosa*, followed by addition of a growth medium and incubation at selected test growing conditions. Following centrifugation, the cleared amplified supernatant is filtered through filter and subjected to another cycle of selective amplification or tested for presence of lytic activity.

The titer of phage in a suspension and the visualization of plaque morphology of bacteriophages of the invention may then be assessed by known methods, for example by plaque counting. Additionally, processing bacteriophages of the invention in various forms (liquid, lyophilized, etc.) for short-, long-, freeze- or any other kind of storage can be carried out by any suitable method as it is well-known in the art (see e.g., Clark, 1962).

The activity of the bacteriophages of the invention can be assessed by methods well-known in the art, such as plaque assay also known as double agar method, based on the growing of bacteriophage with potential host bacteria and followed by assessing their ability to kill the host bacterial cell. In the plaque assay method, the bacteriophage induces lysis of target *P. aeruginosa* strains after a period of incubation in soft agar medium, resulting in zones of clearing on the plate known as plaques.

In a particular embodiment, the invention is related to BP1384 bacteriophage, or any variant thereof. BP1384 bacteriophage, or any variant thereof, can be produced or expanded in e.g., *P. aeruginosa* strain PAO1. BP1384, or any variant thereof, is specific and has lytic activity against LMG24882, LMG24883, LMG24886, LMG24891, LMG24892, LMG24893, LMG24896, LMG24898 and/or LMG24909 strains. BP1384 comprises a genome comprising a sequence as set forth in SEQ ID NO: 1 or having at least 80% identity, more preferably at least 85% identity, and still more preferably 90%, 92%, 94%, 95%, 96%, 97%, 98% or 99% identity to SEQ ID NO: 1. It is also provided an isolated nucleic acid sequence from BP1384 bacteriophage, or variant thereof. The invention also encompasses isolated polypeptides encoded by BP1384 bacteriophage, or variant thereof, or encoded by an isolated nucleic acid sequence from BP1384 bacteriophage of the invention. BP1384 bacteriophage of the invention is also characterized by a PLE below 20, more preferably below 15 and still more preferably of around 6.2.

In another particular embodiment, the invention is related to BP1429 bacteriophage, or any variant thereof. BP1429 bacteriophage, or any variant thereof, can be produced or expanded in e.g., *P. aeruginosa* strain PAO1. BP1429, or any variant thereof, is specific and has lytic activity against LMG24882, LMG24891, LMG24892, LMG24893, LMG24896, LMG24898 and/or LMG24916 strains. BP1429 comprises a genome comprising a sequence as set forth in SEQ ID NO: 2 or having at least 80% identity, more preferably at least 85% identity, and still more preferably 90%, 92%, 94%, 95%, 96%, 97%, 98% or 99% identity to SEQ ID NO: 2. It is also provided an isolated nucleic acid sequence from BP1429 bacteriophage, or variant thereof. The invention also encompasses isolated polypeptides encoded by BP1429 bacteriophage, or variant thereof, or encoded by an isolated nucleic acid sequence from BP1429 bacteriophage of the invention. BP1429 bacteriophage of the invention is also characterized by a PLE below 20, more preferably below 15 and still more preferably of around 0.70.

In still another aspect, the invention is related to BP1430 bacteriophage, or any variant thereof. BP1430 bacteriophage, or any variant thereof, can be produced or expanded in e.g., *P. aeruginosa* strain PAO1. BP1430, or any variant thereof, is specific for and has lytic activity against LMG24882, LMG24883, LMG24891, LMG24892, LMG24893, LMG24896, LMG24898, LMG24901 and/or LMG24918 strains. BP1430 comprises a genome comprising a sequence as set forth in SEQ ID NO: 3 or having at least 80% identity, more preferably at least 85% identity, and still more preferably 90%, 92%, 94%, 95%, 96%, 97%, 98% or 99% identity to SEQ ID NO: 3. It is also provided an isolated nucleic acid sequence from B1430 bacteriophage, or variant thereof. The invention also encompasses isolated polypeptides encoded by BP1430 bacteriophage, or variant thereof, or encoded by an isolated nucleic acid sequence from BP1430 bacteriophage of the invention. BP1430 bacteriophage of the invention is also characterized by a PLE below 20, more preferably below 15 and still more preferably of around 3.

In another aspect, the invention is related to BP1433 bacteriophage, or any variant thereof. BP1433 bacteriophage, or any variant thereof, can be produced or expanded in e.g., *P. aeruginosa* strain PAO1. BP1433, or any variant thereof, is specific and has lytic activity against LMG24882, LMG24883, LMG24886, LMG24887, LMG24891, LMG24892, LMG24893, LMG24896, LMG24896, LMG24905, LMG24909 and/or LMG24916 strains. BP1433 comprises a genome comprising a sequence as set forth in SEQ ID NO: 4 or having at least 80% identity, more preferably at least 85% identity, and still more preferably 90%, 92%, 94%, 95%, 96%, 97%, 98% or 99% identity to SEQ ID NO: 4. It is also provided an isolated nucleic acid sequence from BP1433 bacteriophage, or variant thereof. The invention also encompasses isolated polypeptides encoded by BP1433 bacteriophage, or variant thereof, or encoded by an isolated nucleic acid sequence from BP1433 bacteriophage of the invention. BP1433 bacteriophage of the invention is also characterized by a PLE below 20, more preferably below 15 and still more preferably of around 4.

In another particular embodiment, the invention is related to BP1450 bacteriophage, or any variant thereof. BP1450 bacteriophage, or any variant thereof, can be produced or expanded in e.g., *P. aeruginosa* strain PAO1. BP1450, or any variant thereof, is specific for and has lytic activity against LMG24882, LMG24883, LMG24886, LMG24887, LMG24891, LMG24892, LMG24893, LMG24896, LMG24898, LMG24903, LMG24904, LMG24905, LMG24909 and/or LMG24913 strains. BP1450 comprises a genome comprising a sequence as set forth in SEQ ID NO: 5 or having at least 80% identity, more preferably at least 85% identity, and still more preferably 90%, 92%, 94%, 95%, 96%, 97%, 98% or 99% identity to SEQ ID NO: 5. It is also provided an isolated nucleic acid sequence from BP1450 bacteriophage, or variant thereof. The invention also encompasses isolated polypeptides encoded by BP1450 bacteriophage, or variant thereof, or encoded by an isolated nucleic acid sequence from BP1450 bacteriophage of the invention. BP1450 bacteriophage of the invention is also characterized by a PLE below 20, more preferably below 15 and still more preferably of around 2.

In still another aspect, the invention is related to BP1644 bacteriophage, or any variant thereof. BP1644 bacteriophage, or any variant thereof, can be produced or expanded in e.g., *P. aeruginosa* strain PAO1. BP1644, or any variant thereof, is specific and has lytic activity against LMG24882, LMG24883, LMG24886, LMG24891, LMG24892, LMG24893, LMG24896, LMG24898, LMG24905 and/or LMG24909 strains. BP1644 comprises a genome comprising a sequence as set forth in SEQ ID NO: 6 or having at least 80% identity, more preferably at least 85% identity, and still more preferably 90%, 92%, 94%, 95%, 96%, 97%, 98% or 99% identity to SEQ ID NO: 6. It is also provided an isolated nucleic acid sequence from BP1644 bacteriophage, or variant thereof. The invention also encompasses isolated polypeptides encoded by BP1644 bacteriophage, or variant thereof, or encoded by an isolated nucleic acid sequence from BP1644 bacteriophage of the invention. BP1644 bacteriophage of the invention is also characterized by a PLE below 20, more preferably below 15 and still more preferably of around 1.5.

In another particular embodiment, the invention is related to BP1647 bacteriophage, or any variant thereof. BP1647 bacteriophage, or any variant thereof, can be produced or expanded in, e.g., *P. aeruginosa* strain PAO1. BP1647, or any variant thereof, is specific for and has lytic activity against LMG24882, LMG24883, LMG24891, LMG24892, LMG24893, LMG24896, LMG24898, LMG24903 and/or LMG24916 strains. BP1647 comprises a genome comprising a sequence as set forth in SEQ ID NO: 7 or having at least 80% identity, more preferably at least 85% identity, and still more preferably 90%, 92%, 94%, 95%, 96%, 97%, 98% or 99% identity to SEQ ID NO: 7. It is also provided an isolated nucleic acid sequence from BP1647 bacteriophage, or variant thereof. The invention also encompasses isolated polypeptides encoded by BP1647 bacteriophage, or variant thereof, or encoded by an isolated nucleic acid sequence from BP1647 bacteriophage of the invention. BP1647 bacteriophage of the invention is also characterized by a PLE below 20, more preferably below 15 and still more preferably of around 0.4.

In another particular embodiment, the invention is related to BP1648 bacteriophage, or any variant thereof. BP1648 bacteriophage, or any variant thereof, can be produced or expanded in e.g., *P. aeruginosa* strain PAO1. BP1648, or any variant thereof, is specific for and has lytic activity against LMG24882, LMG24883, LMG24891, LMG24893, LMG24896, LMG24898, and/or LMG24909 strains. BP1648 comprises a genome comprising a sequence as set forth in SEQ ID NO: 8 or having at least 80% identity, more preferably at least 85% identity, and still more preferably 90%, 92%, 94%, 95%, 96%, 97%, 98% or 99% identity to SEQ ID NO: 8. It is also provided an isolated nucleic acid sequence from BP1648 bacteriophage, or variant thereof. The invention also encompasses isolated polypeptides encoded by BP1648 bacteriophage, or variant thereof, or encoded by an isolated nucleic acid sequence from BP1648 bacteriophage of the invention. BP1648 bacteriophage of the invention is also characterized by a PLE below 20, more preferably below 15 and still more preferably of around 2.

In another aspect, the invention is related to BP1649 bacteriophage, or any variant thereof. BP1649 bacteriophage, or any variant thereof, can be produced or expanded in e.g., *P. aeruginosa* strain PAO1. BP1649, or any variant thereof, is specific for and has lytic activity against LMG24882, LMG24883, LMG24886, LMG24887, LMG24891, LMG24892, LMG24893, LMG24896, LMG24898, LMG24905, LMG24909 and/or LMG24913 strains. BP1649 comprises a genome comprising a sequence as set forth in SEQ ID NO: 9 or having at least 80% identity, more preferably at least 85% identity, and still more preferably 90%, 92%, 94%, 95%, 96%, 97%, 98% or 99% identity to SEQ ID NO: 9. It is also provided an isolated nucleic acid sequence from BP1649 bacteriophage, or variant thereof. The invention also encompasses isolated polypeptides encoded by BP1649 bacteriophage, or variant thereof, or encoded by an isolated nucleic acid sequence from BP1649 bacteriophage of the invention. BP1155 bacteriophage of the invention is also characterized by a PLE below 20, more preferably below 15 and still more preferably of around 3.5.

In another particular embodiment, the invention is related to BP1650 bacteriophage, or any variant thereof. BP1650 bacteriophage, or any variant thereof, can be produced or expanded in e.g., *P. aeruginosa* strain PAO1. BP1650, or any variant thereof, is specific for and has lytic activity against LMG24882, LMG24893, LMG24896, LMG24898, LMG24905, and/or LMG24909 strains. BP1650 comprises a genome comprising a sequence as set forth in SEQ ID NO: 10 or having at least 80% identity, more preferably at least 85% identity, and still more preferably 90%, 92%, 94%, 95%, 96%, 97%, 98% or 99% identity to SEQ ID NO: 10. It is also provided an isolated nucleic acid sequence from BP1650 bacteriophage, or variant thereof. The invention also encompasses isolated polypeptides encoded by BP1650 bacteriophage, or variant thereof, or encoded by an isolated nucleic acid sequence from BP1650 bacteriophage of the invention. BP1650 bacteriophage of the invention is also characterized by a PLE below 20, more preferably below 15 and still more preferably of around 14.

In still another aspect, the invention is related to BP1658 bacteriophage, or any variant thereof. BP1658 bacteriophage, or any variant thereof, can be produced or expanded in e.g., *P. aeruginosa* strain PAO1. BP1658, or any variant thereof, is specific for and has lytic activity against LMG24882, LMG24887, LMG24891, LMG24893, LMG24896 and/or LMG24898 strains. BP1658 comprises a genome comprising a sequence as set forth in SEQ ID NO: 11 or having at least 80% identity, more preferably at least 85% identity, and still more preferably 90%, 92%, 94%, 95%, 96%, 97%, 98% or 99% identity to SEQ ID NO: 11. It is also provided an isolated nucleic acid sequence from BP1658 bacteriophage, or variant thereof. The invention also encompasses isolated polypeptides encoded by BP1658 bacteriophage, or variant thereof, or encoded by an isolated nucleic acid sequence from BP1658 bacteriophage of the invention. BP1658 bacteriophage of the invention is also characterized by a PLE below 20, more preferably below 15 and still more preferably of around 3.

In another aspect, the invention is related to BP1661 bacteriophage, or any variant thereof. BP1661 bacteriophage, or any variant thereof, can be produced or expanded in e.g., *P. aeruginosa* strain PAO1. BP1661 or any variant thereof, is specific for and has lytic activity against LMG24882, LMG24883, LMG24886, LMG24891, LMG24892, LMG24893, LMG24896, LMG24898, and/or LMG24909 strains. BP1661 comprises a genome comprising a sequence as set forth in SEQ ID NO: 12 or having at least 80% identity, more preferably at least 85% identity, and still more preferably 90%, 92%, 94%, 95%, 96%, 97%, 98% or 99% identity to SEQ ID NO: 12. It is also provided an isolated nucleic acid sequence from BP1661 bacteriophage, or variant thereof. The invention also encompasses isolated polypeptides encoded by BP1661 bacteriophage, or variant thereof, or encoded by an isolated nucleic acid sequence from BP1661 bacteriophage of the invention. BP1661 bacteriophage of the invention is also characterized by a PLE below 20, more preferably below 15 and still more preferably of around 4.

In still another aspect, the invention is related to BP1662 bacteriophage, or any variant thereof. BP1662 bacteriophage, or any variant thereof, can be produced or expanded in e.g., *P. aeruginosa* strain PAO1. BP1662 or any variant thereof, is specific for and has lytic activity against LMG24883, LMG24891, LMG24892, LMG24893, LMG24896, LMG24898, and/or LMG24916 strains. BP1662 comprises a genome comprising a sequence as set forth in SEQ ID NO: 13 or having at least 80% identity, more preferably at least 85% identity, and still more preferably 90%, 92%, 94%, 95%, 96%, 97%, 98% or 99% identity to SEQ ID NO: 13. It is also provided an isolated nucleic acid sequence from BP1662 bacteriophage, or variant thereof. The invention also encompasses isolated polypeptides encoded by BP1662 bacteriophage, or variant thereof, or encoded by an isolated nucleic acid sequence from BP1662 bacteriophage of the invention. BP1662 bacteriophage of the invention is also characterized by a PLE below 20, more preferably below 15 and still more preferably of around 1.

Nucleic Acids and Polypeptides

The invention relates to a nucleic acid contained in a bacteriophage of the invention, or any fragment of such a nucleic acid. The term fragment designates, more preferably, a fragment containing (or consisting of) an open reading frame. The nucleic acid may be DNA or RNA, single- or double-stranded.

The nucleic acid can be isolated from the deposited bacteriophages, or produced using recombinant DNA technology (e.g., polymerase chain reaction (PCR) amplification, cloning), enzymatic or chemical synthesis, or combinations thereof, according to general techniques known per se in the art. Also included are homologous sequences and fragments thereof including, but not limited to, natural allelic variants and modified nucleic acid sequences in which nucleotides have been inserted, deleted, substituted, and/or inverted.

In a particular embodiment, the invention relates to a nucleic acid comprising a sequence selected from any one of SEQ ID NOs: 1-13, or a sequence having at least 95%, 96%, 97%, 98%, 99% or more sequence identity to any one of SEQ ID NOs: 1-13.

In another particular embodiment, the invention relates to a nucleic acid comprising the sequence of a fragment of a sequence selected from any one of SEQ ID NOs: 1-13, or a fragment of a sequence having at least 95%, 96%, 97%, 98%, 99% or more sequence identity to any one of SEQ ID NOs: 1-13, said fragment comprising an open reading frame or a regulatory element such as a promoter.

The nucleic acid of the invention can be in free form, or cloned in a vector.

In a further aspect, the invention also relates to an isolated polypeptide encoded by a nucleic acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13. The polypeptides may be produced by techniques known per se in the art such as synthesis, recombinant technology, or combinations thereof. The polypeptides may be isolated or purified, and used as antibacterial agents or as reagents for in vitro analyses.

Compositions of the Invention

One aspect of the invention relates to compositions comprising at least one bacteriophage as described above, more preferably at least 2 or more and, optionally, a pharmaceutically or veterinary acceptable excipient. As described, the bacteriophages of the invention have very potent lytic activity against *P. aeruginosa* strains. Combinations of these bacteriophages may be produced to expand the host spectrum and produce highly effective antibacterial compositions.

More particularly, the invention relates to an antibacterial composition comprising at least two bacteriophages having lytic activity against a *Pseudomonas aeruginosa* (*P. aeruginosa*) strain, said at least two bacteriophages being selected from the bacteriophages having a genome comprising a nucleotide sequence of any one of SEQ ID NOs: 1 to 13 or a sequence having at least 90% identity thereto, preferably at least 91%, 92%, 93%, 94%, 95%, 96%, 97%, 98% or 99% identity thereto.

In a preferred embodiment, the compositions of the invention comprise at least three, even more preferably at least four distinct bacteriophages selected from the bacteriophages having a genome comprising a nucleotide sequence of any one of SEQ ID NOs: 1 to 13 or a sequence having at least 90% identity thereto, preferably at least 91%, 92%, 93%, 94%, 95%, 96%, 97%, 98% or 99% identity thereto. Compositions of the invention may comprise at least 5, 6, 7, 8, 9, 10, 11, 11, 12 or all of the 13 distinct types of bacteriophages as disclosed above.

One aspect of the invention is related to a composition at least one bacteriophage selected from BP1384, BP1429, BP1430, BP1433, BP1450, BP1644, BP1647, BP1648, BP1649, BP1650, BP1658, BP1661 and/or BP1662, or variants thereof.

The invention also concerns a composition comprising at least two distinct bacteriophages selected from BP1384, BP1429, BP1430, BP1433, BP1450, BP1644, BP1647, BP1648, BP1649, BP1650, BP1658, BP1661 and/or BP1662, or variants thereof.

In a particular embodiment, a composition of the invention comprises BP1384 in combination with at least one further bacteriophage selected from BP1429, BP1430, BP1433, BP1450, or BP1644.

In another particular embodiment, a composition of the invention comprises BP1384 in combination with at least one further bacteriophage selected from BP1450 and BP1647.

In another particular embodiment, a composition of the invention comprises BP1430 in combination with at least one further bacteriophage selected from BP1450, BP1644, BP1649 and BP1661.

In another particular embodiment, the composition comprises BP1433 in combination with at least one further bacteriophage selected from BP1450, BP1647, BP1648, BP1650 and BP1658.

In another preferred embodiment, the composition comprises BP1384 in combination with at least one further bacteriophage selected from BP1429, BP1647, BP1649 and BP1662.

The invention also relates to a composition comprising a combination of all of the bacteriophages BP1384, BP1429, BP1430, BP1433, BP1450, BP1644, BP1647, BP1648, BP1649, BP1650, BP1658, BP1661 and/or BP1662, or variants thereof.

Specific examples of compositions of the invention comprise:

a bacteriophage having a genome comprising a nucleotide sequence of SEQ ID NO: 1 or a sequence having at least 90% identity thereto, and a bacteriophage having a genome comprising a nucleotide sequence of SEQ ID NO: 4 or a sequence having at least 90% identity thereto;

a bacteriophage having a genome comprising a nucleotide sequence of SEQ ID NO: 1 or a sequence having at least 90% identity thereto, and a bacteriophage having a genome comprising a nucleotide sequence of SEQ ID NO: 5 or a sequence having at least 90% identity thereto;

a bacteriophage having a genome comprising a nucleotide sequence of SEQ ID NO: 3 or a sequence having at least 90% identity thereto, and a bacteriophage having a genome comprising a nucleotide sequence of SEQ ID NO: 9 or a sequence having at least 90% identity thereto;

a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto;

a bacteriophage having a genome comprising a nucleotide sequence of SEQ ID NO: 3 or a sequence having at least 90% identity thereto, and a bacteriophage having a genome comprising a nucleotide sequence of SEQ ID NO: 10 or a sequence having at least 90% identity thereto;

a bacteriophage having a genome comprising a nucleotide sequence of SEQ ID NO: 1 or a sequence having at least 90% identity thereto, and a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto;

a bacteriophage having a genome comprising a nucleotide sequence of SEQ ID NO: 1 or a sequence having at least 90% identity thereto, and a bacteriophage having a genome comprising a nucleotide sequence of SEQ ID NO: 3 or a sequence having at least 90% identity thereto, and a bacteriophage having a genome comprising a nucleotide sequence of SEQ ID NO: 5 or a sequence having at least 90% identity thereto; or a bacteriophage having a genome comprising a nucleotide sequence of SEQ ID NO: 1 or a sequence having at least 90% identity thereto, and a bacteriophage having a genome comprising a nucleotide sequence of SEQ ID NO: 3 or a sequence having at least 90% identity thereto, and a bacteriophage having a genome comprising a nucleotide sequence of SEQ ID NO: 9 or a sequence having at least 90% identity thereto.

A specific embodiment of the invention relates to a composition comprising:

a bacteriophage having a genome comprising a nucleotide sequence of SEQ ID NO: 1 or a sequence having at least 90% identity thereto;

a bacteriophage having a genome comprising a nucleotide sequence of SEQ ID NO: 2 or a sequence having at least 90% identity thereto;

a bacteriophage having a genome comprising a nucleotide sequence of SEQ ID NO: 3 or a sequence having at least 90% identity thereto;

a bacteriophage having a genome comprising a nucleotide sequence of SEQ ID NO: 4 or a sequence having at least 90% identity thereto;

a bacteriophage having a genome comprising a nucleotide sequence of SEQ ID NO: 5 or a sequence having at least 90% identity thereto;

a bacteriophage having a genome comprising a nucleotide sequence of SEQ ID NO: 6 or a sequence having at least 90% identity thereto;

a bacteriophage having a genome comprising a nucleotide sequence of SEQ ID NO: 7 or a sequence having at least 90% identity thereto;

a bacteriophage having a genome comprising a nucleotide sequence of SEQ ID NO: 8 or a sequence having at least 90% identity thereto;

a bacteriophage having a genome comprising a nucleotide sequence of SEQ ID NO: 9 or a sequence having at least 90% identity thereto;

a bacteriophage having a genome comprising a nucleotide sequence of SEQ ID NO: 10 or a sequence having at least 90% identity thereto;

a bacteriophage having a genome comprising a nucleotide sequence of SEQ ID NO: 11 or a sequence having at least 90% identity thereto;

a bacteriophage having a genome comprising a nucleotide sequence of SEQ ID NO: 12 or a sequence having at least 90% identity thereto; and a bacteriophage having a genome comprising a nucleotide sequence of SEQ ID NO: 13 or a sequence having at least 90% identity thereto.

The compositions of the invention may further comprise additional antibacterial agents, particularly other bacteriophages having distinct host specificity.

Preferred compositions of the invention are lytic against antibiotic-resistant *P. aeruginosa* strains.

Further preferred compositions of the invention are lytic against more that 90% of all bacterial strains of the LMG collection, obtained from the well-known BCCM/LMG Bacteria Collection. This collection is accessible via Worldwide Website: cabri.org/CABRI/srs-doc/bccm_lmg.info.html.

The antibacterial compositions of the invention may be in various forms, such as liquid, semi-liquid, solid or lyophilized formulations.

The compositions of the invention may comprise any effective amount of the selected bacteriophage(s). Preferably, they comprise between $10^{e4}$ and $10^{e12}$ PFU of each of said bacteriophages, preferably between $10^{e5}$ and $10^{e10}$ PFU. The relative amounts of each type of bacteriophage in a composition of the invention may be adjusted by a skilled artisan. Typically, when the antibacterial composition comprises several (n) distinct bacteriophages as defined above, the total relative amount % A of each bacteriophage in the composition is more preferably % $A=(100/n_i)\times V$, wherein $n_i$ represents the number of distinct types of bacteriophages and V is a variability factor comprised between 0.2 and 5. Most preferably, V is comprised between 0.3 and 3, even more preferably between 0.5 and 2, generally between 0.8 and 1.5. In a preferred typical embodiment, each type of bacteriophage is present in a composition of the invention in approximately equal relative amounts.

The compositions of the invention preferably comprise a suitable diluent or carrier, such as a pharmaceutically or veterinary acceptable excipient or carrier. Compositions according to the present invention may include any excipient or carrier, such as thickeners, diluents, buffers, preservatives, surface active agents and the like, in addition to the bacteriophage(s) of choice. Such includes physiologically acceptable solutions or vehicles that are harmless or do not cause any significant specific or non-specific immune reaction to an organism or do not abrogate the biological activity of the bacteriophage. For liquid formulation, saline, sterile water, Ringer's solution, buffered physiological saline, albumin infusion solution, dextrose solution, maltodextrin solution, glycerol, ethanol, and mixtures thereof may be used as a pharmaceutically or veterinary acceptable excipient or carrier. If appropriate, other conventional additives such as thickeners, diluents, buffers, preservatives, surface active agents, antioxidants and bacteriostatic agents may be added. Further, diluents, dispersants, surfactants, binders and lubricants may be additionally added to the composition to prepare injectable formulations such as aqueous solutions, suspensions, and emulsions, oral formulations such as pills, capsules, granules, or tablets, or powdered formulations. Formulations for topical administration may include, band aids, dressings, patches, films, ointments, lotions, creams, gels, drops, suppositories, sprays, tampons, sanitary towels, liquids and powders. Formulations for decontamination or for medical use may also include aerosols or sprays.

The compositions of the invention may be used in the medical field, including the human or veterinary medical areas, for e.g. the treatment of an infection in a mammal or for improving a subject's condition. The compositions may be used to kill *P. aeruginosa* bacteria in an organism, for treating an infection. The composition may also be used for improving the condition of a mammal by modifying the microbial flora in said mammal. In particular, the compositions of the invention can specifically remove *P. aeruginosa* strains on the skin or mucous membranes of a mammal, thus modifying its microbial flora and restoring a proper balance.

In a particular embodiment, the invention also relates to a method for treating an infection in a mammal comprising the administration to said mammal of a composition or bacteriophage or nucleic acid or polypeptide as defined above. In a particular embodiment the method comprises administering at least one, preferably at least two, even more preferably at least three bacteriophages selected from BP1384, BP1429, BP1430, BP1433, BP1450, BP1644, BP1647, BP1648, BP1649, BP1650, BP1658, BP1661 and/or BP1662, or variants thereof.

The invention also relates to the use of a composition, bacteriophage, nucleic acid or polypeptide as described for the manufacture of a medicament for treating an infection in a mammal, or for restoring microbial flora in said mammal.

The compositions or agents of the invention may be administered by any convenient route, including intravenous, oral, transdermal, subcutaneous, mucosal, intramuscular, intrapulmonary, intranasal, parenteral, rectal, vaginal and topical. In a preferred embodiment, the bacteriophages or compositions are administered by topical route, e.g., by application on the skin of a subject. The compositions may be administered directly or indirectly, e.g., via a support. In this regard, the compositions may, for example, be applied or sprayed to the afflicted area. Compositions of the invention can also be administered by oral or parenteral routes. The dosage suitable for applying, spraying, or administering the compositions of the present invention can be adjusted by the skilled person depending on a variety of factors including formulation, mode of administration, age, weight, sex, condition, diet of the mammal being treated at the time of administration, route of administration, and reaction sensitivity. A physician having ordinary skill in the art can readily determine and prescribe the effective amount of the composition required.

The dosing can also be adjusted by the skilled person so that a lytic activity against antibiotic-resistant *P. aeruginosa* strains is obtained. An efficient dose to obtain a lytic activity in vivo typically includes a concentration of at least $10^{e2}$ PFU/ml, preferably from about $10^{e2}$ to $10^{e12}$ PFU/ml, depending on the administration route. Administration may be performed only once or, if needed, repeated.

The compositions of the invention may be administered to treat *P. aeruginosa* infections, typically of the respiratory tract, urinary tract, burns, wounds, ear, skin, or soft tissues, or gastrointestinal or post-surgical infections.

As shown in the Examples section, the bacteriophages and compositions of the invention are able to selectively kill *P. aeruginosa* bacteria in vitro or in vivo. The compositions can destroy mixtures of different *P aeruginosa* bacteria, even in vivo, even at low dosage. Furthermore, the compositions of the invention are effective at killing bacteria embedded in biofilms, which is particularly important for pathogenic bacteria. Also, the compositions and bacteriophages of the invention are strictly unable to affect mammalian cells, and are therefore specific and devoid of side effects in vivo.

The invention also relates to the use of a composition, bacteriophage, nucleic acid or polypeptide of the invention for decontaminating a material. Due to their potent antibacterial effect, and to their ability to even compromise the integrity of a bacterial biofilm, the compositions of the invention can be used as decontaminating agent, to eliminate or at least cause a reduction in bacterial numbers on a material. Such methods may be applied for the treatment of a variety of biological or non-biological surfaces in both medical and non-medical contexts, including solid materials or devices such as, for example, contact lenses, surfaces of devices to be implanted into the body, pipes, ducts, laboratory vessels, textiles, etc.

Diagnostic/Predictive Tests of the Invention:

The invention also concerns a method for predicting or determining the efficacy of a bacteriophage therapy in a subject, wherein the method comprises a step of determining a lytic activity of one or more bacteriophages selected from BP1384, BP1429, BP1430, BP1433, BP1450, BP1644, BP1647, BP1648, BP1649, BP1650, BP1658, BP1661 and/or BP1662 to a *P. aeruginosa* strain from a sample from said subject, such lytic activity being indicative of an efficient treatment. In a preferred aspect, the method further optionally comprises a step of treating said subject by one or more bacteriophages having a lytic activity to a *P. aeruginosa* strain from a sample of said subject.

In another aspect, the invention provides a method for selecting a subject or determining whether a subject is susceptible to benefit from a bacteriophage therapy, wherein the method comprises the step of determining a lytic activity of one or more bacteriophages selected from BP1384, BP1429, BP1430, BP1433, BP1450, BP1644, BP1647, BP1648, BP1649, BP1650, BP1658, BP1661 and/or BP1662 to a *P. aeruginosa* strain from a sample of said subject, a lytic activity of one or more bacteriophages of the invention to at least one *P. aeruginosa* strain indicating a responder subject.

Another object of the invention relates to a method for predicting the response of a subject to a bacteriophage therapy, wherein the method comprises the step of determining a lytic activity of one or more bacteriophage selected from BP1384, BP1429, BP1430, BP1433, BP1450, BP1644, BP1647, BP1648, BP1649, BP1650, BP1658, BP1661 and/or BP1662 to a *P. aeruginosa* strain from a sample of said subject, a lytic activity of one or more bacteriophage of the invention to at least one *P. aeruginosa* strain being indicative of a good response to said therapy.

Further aspects and advantages of the invention will be disclosed in the following experimental section, which is illustrative only.

EXAMPLES

Materials and Methods
Phage Isolation and Preparation

MDR *P. aeruginosa* bacteria were used for isolating and enriching each virulent bacteriophage from environmental water. Environmental samples and overnight culture of bacteria in Luria Bertani (LB) were mixed and incubated at 37° C. for 24 h with shaking to enrich specific bacteriophages. At the end of incubation, drops of chloroform were added to the culture. The culture was spun down at 11,000 g for 5 minutes to remove bacterial cells and debris. The supernatant was subjected to 0.2 μm filter to remove the residual bacterial cells. The enriched phage solution was plated on LB agar medium with *P. aeruginosa* embedded. Plaques formed on the plates after 24 h incubation at 37° C. Single plaque was picked out for subsequent phage purification and amplification. The phage was then stored at 4° C. in a suspension in LB broth or physiological saline.

The titer of phage in a suspension was estimated by plaque counting (Postic, 1961). 10-fold dilutions of a suspension were delivered on a dried lawn of the propagating strain. The plates were read after overnight incubation. The plaque-counting method also permitted visualization of plaque morphology.

Host Range Determination

The host ranges of bacteriophages were determined among a collection of 20 *P. aeruginosa* from the LMG collection. $10^9$ bacterial cells were mixed with melted agar and this mixture was poured on solid agar to make double layer agar plates. After solidification, isolated bacteriophage stock solutions were spotted on each plate with different bacterium strain. After allowing 20 min for the spots to be absorbed, the plates were inverted and incubated for 24 h at 37° C. before the degree of lysis was recorded (Postic, 1961; Yang, 2010).

Electron Microscopy

Electron micrographs of each phage were taken with a transmission electron microscope.

Sequencing, Analysis and Annotation of Phage Genomes

To isolate phage DNA, phages were propagated as described above. Phage DNA was isolated by extraction with phenol:chloroform:isoamyl alcohol (25:24:1, V/V), ethanol precipitation and resolution in water. Whole genome sequencing was done and the BLAST algorithm was used to determine the similarity to described genes in the National Center for Biotechnology Information (NCBI) database. The genomes were scanned for potential open reading frames (ORFs).

Example 1: Bacteriophage-Host Characteristics and Kinetics

One-step growth experiments were carried out according to the previous descriptions to determine first the productive lytic time, adsorption rate then the phage burst size. To determine the adsorption rate samples were taken at different time intervals to analyze the free phage particles in the solutions. For productive time and phage burst size determination, *P. aeruginosa* bacteria were mixed with phage solutions and phages were allowed to adsorb for 15 min. The mixture was subjected to centrifugation immediately at 5000 rpm for 10 min to remove free phage particles. The pellet was resuspended in 5 fresh LB medium and the culture was continuously incubated at 37° C. Samples were taken at 3 min intervals and phage titre was determined. These results permitted to calculate the number of phages produced per bacteria (burst size), the productive time and the productive lytic effect (PLE), as shown in Table 5 below.

TABLE 4

| Phage | Productive lytic time (min) | Adsorption rate (ml−1min−1) | BURST SIZE (PFU per bacterium) | PLE (PFU per bacterium per min) |
|---|---|---|---|---|
| 1384 | 80 | 8.64E−09 | 499 | 6.24 |
| 1429 | 70 | 9.16E−09 | 49 | 0.70 |
| 1430 | 60 | 1.66E−08 | 166 | 2.76 |
| 1433 | 100 | 2.72E−09 | 399 | 3.99 |
| 1450 | 100 | 1.07E−08 | 199 | 1.99 |
| 1644 | 70 | 8.35E−09 | 99 | 1.41 |
| 1647 | 90 | 2.34E−08 | 32 | 0.36 |
| 1648 | 100 | 2.70E−09 | 199 | 1.99 |
| 1649 | 100 | 1.10E−08 | 332 | 3.32 |
| 1650 | 70 | 3.47E−09 | 999 | 14.27 |
| 1658 | 90 | 1.61E−08 | 249 | 2.77 |
| 1661 | 90 | 7.11E−09 | 332 | 3.69 |
| 1662 | 90 | 9.16E−09 | 99 | 1.10 |

These results show that all phages have potent viral production capacity and absorption rates. Most phages have a PLE below 7, which demonstrates a remarkable profile. Phages 1429 and 1647 are particularly effective in this regard. In addition, the different PLE and adsorption times permit to create cocktails with selected variability.

Example 2: Preparation of Cocktail Compositions

The following cocktail compositions are constituted, each comprising between 10-9 and 10-11 pfu of each bacteriophage:

TABLE 5

| Cocktail | Phages |
|---|---|
| I | P1384 + P1433 |
| II | P1384 + P1450 |
| III | P1430 + P1649 |
| IV | P1430 + P1433 |
| V | P1430 + P1650 |
| VI | P1384 + P1430 + P1433 |
| VII | P1384 + P1430 + P1450 |
| VIII | P1384 + P1430 + P1649 |

The following additional two cocktail compositions comprising all of the various phages are constituted, covering the most important diversity of *P. aeruginosa* species:

| Cocktail composition A: | | | | | | | |
|---|---|---|---|---|---|---|---|
| Phage | | | | | | | |
| 1384 | 1429 | 1430 | 1433 | 1450 | 1644 | 1647 | 1648 |
| titer 4.00E+10 | 1.23E+09 | 5.45E+08 | 8.33E+10 | 8.91E+10 | 9.09E+08 | 2.00E+09 | 3.09E+09 |

| Phage | | | | |
|---|---|---|---|---|
| 1649 | 1650 | 1658 | 1661 | 1662 |
| Titre 9.00E+09 | 9.45E+08 | 1.91E+09 | 1.14E+09 | 3.55E+08 |

| Cocktail composition B: | | | | | | | |
|---|---|---|---|---|---|---|---|
| phage | | | | | | | |
| 1384 | 1429 | 1430 | 1433 | 1450 | 1644 | 1647 | 1648 |
| Titre 1.60E+11 | 2.00E+11 | 2.00E+11 | 1.20E+11 | 8.00E+10 | 1.00E+11 | 1.00E+08 | 1.00E+09 |

| | phage | | | | |
|---|---|---|---|---|---|
| | 1649 | 1650 | 1658 | 1661 | 1662 |
| Titre | 1.00E+11 | 2.20E+11 | 8.00E+10 | 1.00E+11 | 6.00E+07 |

Example 3: Sensitivity of Bacteria to Bacteriophage Cocktails of the Invention

Various strains of bacteria were tested with the bacteriophage cocktails of the invention at $2.10^9$ bacteriophages/ml. Different bacterial concentrations were plated on the bacteriophage cocktail at $2.10^9$ bacteriophages/ml and incubated 24 h at 37° C.

Cocktails are tested on the 22 distinct *P. aeruginosa* bacteria listed in Tables 2 and 3. The % of bacteria species sensitive to the cocktails are listed in Table 6 below:

TABLE 6

| Cocktail | % Killed *P. aeruginosa* species |
|---|---|
| I | 73% |
| II | 82% |
| III | 91% |
| IV | 86% |
| V | 77% |
| VI | 86% |
| VII | 95% |
| VIII | 95% |
| A | 100% |
| B | 100% |

TABLE 7

| Bacteria | Rate (bacteria/ml) |
|---|---|
| LMG 24891 | 1.00E−05 |
| LMG 24945 | 5.80E−06 |
| LMG 24970 | 1.00E−05 |
| LMG 25082 | 4.60E−06 |
| LMG 25131 | 9.00E−06 |
| LMG 25194 | 9.00E−06 |

All tested bacteria are sensitive to compositions of the invention.

Example 4: Cocktail Specificity

The cocktail specificity was confirmed by testing on ten bacteria species, including *Escherichia coli, Acinetobacter baumannii, Enterobacter aerogenes* C, *Enterobacter asburiae, Enterobacter cloacae, Klebsiella pneumoniae, Proteus mirabilis, Staphylococcus aureus, Stenotrophomonasmaltophilia*, and *Serratia marcescens*.

Table 8 summarizes lytic activity observed for each bacteriophage used independently or in combination as a cocktail of 13 bacteriophages.

| | Phage PYO | 1384 | 1429 | 1430 | 1433 | 1450 | 1644 | 1647 | 1648 | 1649 | 1650 | 1658 | 1661 | 1662 | Cocktail 13 phages |
|---|---|---|---|---|---|---|---|---|---|---|---|---|---|---|---|
| *Pseudomonas aeruginosa* | SH 85 | | +/− | +/− | +/− | +/− | +/− | | + | +/− | +/− | +/− | + | | + |
| | SH 224 | | | | | + | | | + | | | + | +/− | + | + |
| *E. coli* | SH 213 | | | | | | | | | | | | | | − |
| | SH 141 | | | | | | | | | | | | | | − |
| *Acinebacter baumanii* | SH 32 | | | | | | | | | | | | | | − |
| | SH 34 | | | | | | | | | | | | | | − |
| *Enterobacter aerogenes* C | SH 97 | | | | | | | | | | | | | | − |
| | SH 98 | | | | | | | | | | | | | | − |
| *Enterobacter asburiae* | SH 74 | | | | | | | | | | | | | | − |
| *Enterobacter cloacae* | SH 111 | | | | | | | | | | | | | | − |
| | SH 121 | | | | | | | | | | | | | | − |
| *Enterobacter amnigenus* | SH 26 | | | | | | | | | | | | | | − |
| *Klebsiella pneumoniae* | SH 89 | | | | | | | | | | | | | | − |
| | SH 283 | | | | | | | | | | | | | | − |
| *Proteus mirabilis* | SH 82 | | | | | | | | | | | | | | − |
| *S. aureus* (meti R) | SH 14 | | | | | | | | | | | | | | − |
| | SH 129 | | | | | | | | | | | | | | − |
| *Stenotrophomonas maltophila* | SH 286 | | | | | | | | | | | | | | − |
| | SH 290 | | | | | | | | | | | | | | − |
| *Serratia marcescens* | SH 314 | | | | | | | | | | | | | | − |

Bacteria were enumerated and used to the calculation of resistance rate (number of bacteria after incubation/number of bacteria plated). Resistance rates with a cocktail comprising the 13 different types of bacteriophages are shown in Table 7 below:

The above table clearly show that no lytic activity on bacteria other than *P. aeruginosa* strain occurred. The bacteriophages and cocktail of the invention are therefore highly specific for *P. aeruginosa* strains.

Example 5: Efficiency of Bacteriophages on *P. aeruginosa* Strain In Vitro

Several strains of the LMG collection were chosen to represent the genetic diversity of *P. aeruginosa* and various forms of antibiotic resistance. Strains were either sensitive or resistant to one or several antibiotics, as described in Table 9. They were grown individually or in combination with 2 to 8 strains. The bacteriophage cocktail was added at an MOI of 1 to $10^{e-6}$, i.e. at a dilution ratio (bacteria/phage) of 1 to 1 million.

TABLE 9

Information about the bacterial strains

| LMG No. | Country | Year | Source | Sero-type | Class ATB resistance |
|---|---|---|---|---|---|
| LMG 24891 | France | 1882-1918 | Surgical bandage | 11 | 1 |
| LMG 24893 | Greece | 1994 | Sputum | 11 | 2 |
| LMG 24909 | Colombia | 2003 | Peritoneal fluid | 12 | 0 |
| LMG 24988 | Turkey | 1997 | Burn | 8 | 3 |
| LMG 24992 | UK | 2003 | CF-patient | NT | 4 |
| LMG 25041 | The Philippines | 1993 | Wound | NT | 2 |
| LMG 25049 | France | 1882-1918 | Wound | 6 | 1 |
| LMG 25140 | Panama | 2006 | Wound | 11 | 5 |

The results are presented in FIG. 1 and in Table 10.

TABLE 10

Efficiency of bacteriophage cocktail obtained in vitro on *P. aeruginosa* mixture at $2.10^{e7}$ cfu/ml and at various dilutions

| | Mix of: | | | | | |
|---|---|---|---|---|---|---|
| | MOI 1 | MOI 0.1 | MOI 0.01 | MOI 0.001 | MOI 0.0001 | MOI 0.000001 |
| 1 bacterium | ++ | ++ | ++ | ++ | ++ | ++ |
| 2 bacteria | ++ | ++ | ++ | ++ | ++ | ++ |
| 3 bacteria | ++ | ++ | + | + | + | + |
| 4 bacteria | ++ | ++ | + | +/− | +/− | +/− |
| 5 bacteria | ++ | + | + | +/− | +/− | |
| 6 bacteria | ++ | + | + | +/− | +/− | |
| 7 bacteria | ++ | + | + | +/− | +/− | |
| 8 bacteria | ++ | + | +/− | +/− | | |

The compositions of the invention are able to kill a mixture of 8 distinct strains of *P. aeruginosa* bacteria together. The cocktail remains efficient against 8 strains at a dilution of 1/1000.

Example 6: Efficiency of Bacteriophages on *P. aeruginosa* Strain In Vivo

An isolated Is580 strain, collected from a burned patient in 1997, was used for the following experiments.

Is580 strain is resistant to ampicillin, AMC, PIP, CEF, CXM, axetil CXM, FOX, CPD, CTX, CAZ, GEN, TOB, OFX, NIT, and SXT.

SKH1 mouse (or hairless mouse) was used as mouse model of *P. aeruginosa* infection.

Modus Operandi: (See Table 11 Below):
Mice were immunodepressed by 3 IP injections of 1.5 mg of cyclophosphamide (Cy), every 2 days from Day −3 before infection.
Mice were burned on skin by 2 μl of liquid yperite at 30 mg/kg.
Infection two days after the burn by subcutaneous injection of a bacterium suspension in burned site.

TABLE 11

| | Day | | | | |
|---|---|---|---|---|---|
| | −3 | −2 | −1 | 0 | 1 |
| Injection route | 1.5 mg Cy IP | Burn Yperite | 1.5 mg Cy IP | Infection SC $10^7$ cfu | 1.5 mg Cy IP |
| PHAGE | | | | SC injection of cocktail (100 μl, i.e. $10^8$ PFU) 6 h post-infection | |

Cocktail compositions were prepared according to Example 1 and compresses soaked of bacteriophages cocktail at $10^{e7}$ phages/ml were applied at Day 0.

Figure 2:
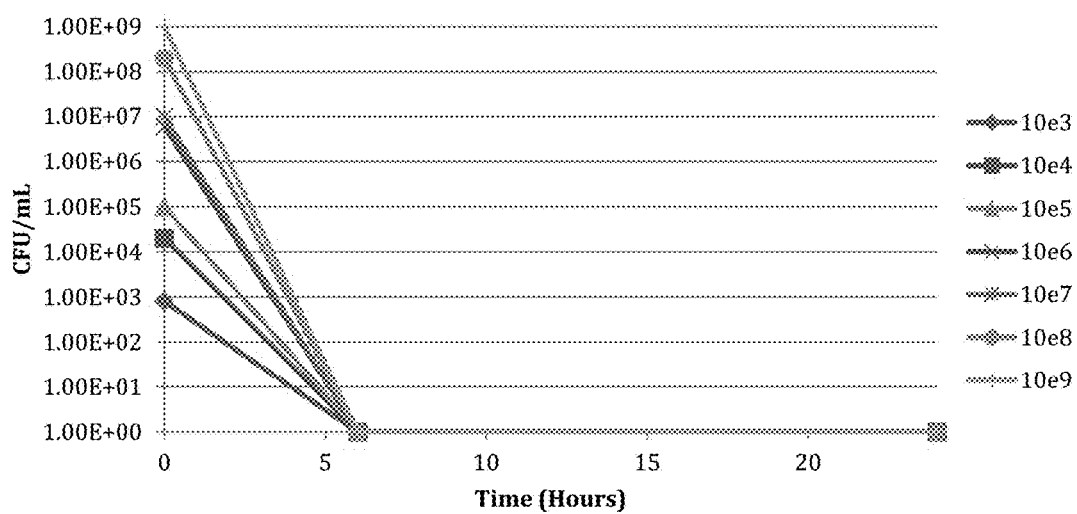
FIG. 2: In vivo efficacy of Bacteriophages of the invention on various combinations of P. aeruginosa strains.

Various concentrations of *P. aeruginosa* strains were tested with 100 μl of bacteriophage cocktail. As shown on FIG. 2, all *P. aeruginosa* strains were killed 6 h post-treatment.

Figure 3:
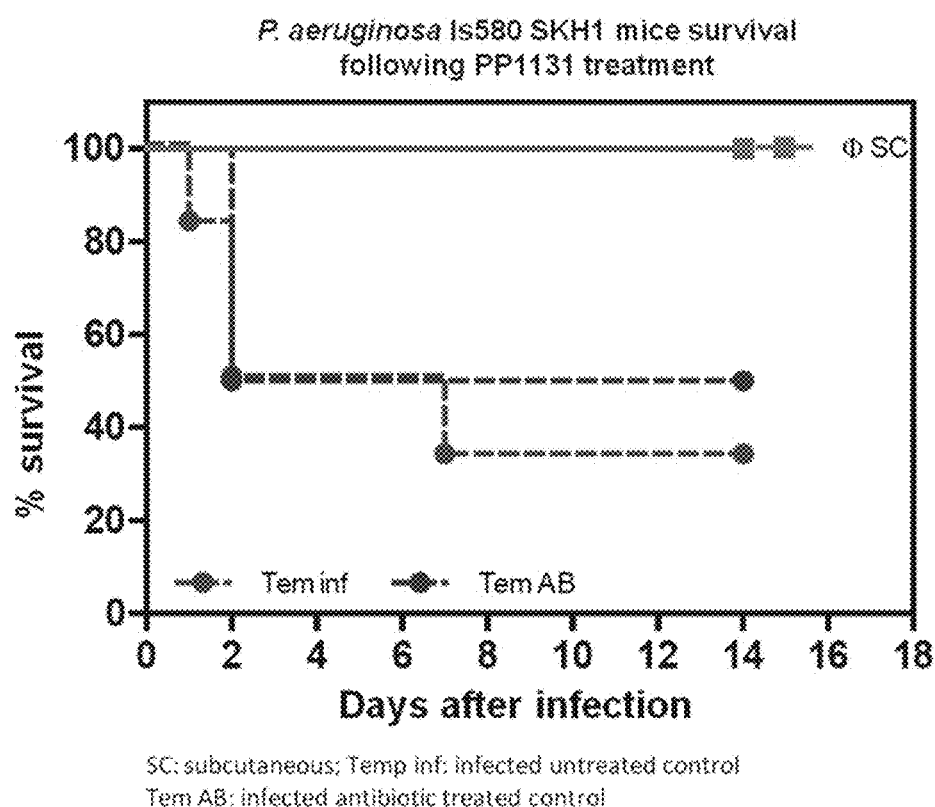
FIG. 3: Efficacy of bacteriophages of the invention in vivo on Is580 *P. aeruginosa* strain-mediated infection.

Upon administration of Is580 *P. aeruginosa* strain by subcutaneous injection to SKH1 mice, only 35% of mice survived in the absence of further treatment. In the mice treated by injection of a bacteriophage cocktail as presented in Table 10 above, a remarkable survival rate was observed (see FIG. 3): 100% survival for SKH1 mice treated subcutaneously, 16 days after infection. By comparison, a 50% survival was observed for SKH1 mice treated by antibiotic 2 days after infection.

Accordingly, the compositions of the invention can treat an infection in vivo and can induce a 100% survival rate in infected mice.

REFERENCES

Clark W A, 1962, Appl Microbiol. Comparison of several methods for preserving bacteriophages. 1962 September; 10:466-71.

Drulis-Kawa Z, Majkowska-Skrobek G, Maciejewska B, Delattre A S, Lavigne R, 2012, Learning from bacteriophages—advantages and limitations of phage and phage-encoded protein applications. Curr. Protein Pept. Sci. 13(8):699-722.

Fordos J. 1859. Recueil des travaux de la Societé d'Emulation pour les Sciences Pharmaceutiques, vol 3 Societé d'Emulation pour les Sciences Pharmaceutiques, Paris, France.

Freeman L. 1916. Chronic general infection with the *Bacillus pyocyaneus*. Ann. Surg. 64:195-202.

Gang R K, Bang R L, Sanyal S C, Mokaddas E, Lari A R. 1999. *Pseudomonas aeruginosa septicaemia* in burns. Burns 25:611-616.

Jones A M, et al. 2010. Clinical outcome for cystic fibrosis patients infected with transmissible *Pseudomonas aeruginosa*: an 8-year prospective study. Chest 137:1405-1409.

Kang C I, et al. 2005. Bloodstream infections caused by antibiotic-resistant gram-negative bacilli: risk factors for mortality and impact of inappropriate initial antimicrobial therapy on outcome. Antimicrob. Agents Chemother. 49:760-766.

Micek S T, et al. 2005. *Pseudomonas aeruginosa* bloodstream infection: importance of appropriate initial antimicrobial treatment. Antimicrob. Agents Chemother. 49:1306-1311.

Strateva T. and Yordanov D. 2009. *Pseudomonas aeruginosa*—a phenomenon of bacterial resistance. Journal of Medical Microbiology 58, 1133-1148.

Weinbauer M G. Ecology of prokaryotic viruses. FEMS Microbiol Rev 2004; 28:127-81.

Williams E P, Cameron K. 1894. Infection by the *Bacillus pyocyaneus* a cause of infantile mortality. Public Health Pap. Rep. 20:355-360.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10260051B2). An electronic copy of the "Sequence Listing" will also be available from the USPTO upon request and payment of the fee set forth in 37 CFR 1.19(b)(3).

We claim:

1. A method of treating a mammal comprising the administration to said mammal of at least one bacteriophage having lytic activity to a *Pseudomonas aeruginosa* (*P. aeruginosa*) strain, wherein said at least one bacteriophage has a genome comprising the nucleotide sequence of SEQ ID NO: 5 or a sequence having at least 98% identity thereto.

2. The method of claim 1, wherein said at least one bacteriophage has a genome comprising the nucleotide sequence of SEQ ID NO: 5 or a sequence having at least 99% identity thereto.

3. The method of claim 1, wherein said at least one bacteriophage has a genome comprising the nucleotide sequence of SEQ ID NO: 5.

4. The method of claim 1, further comprising the combined or separate administration to said mammal of at least one additional bacteriophage.

5. The method of claim 4, wherein said at least one additional bacteriophage has lytic activity to a *P. aeruginosa* strain and has a genome comprising a nucleotide sequence of any one of SEQ ID NOs: 1 to 4 and 6 to 13 or a sequence having at least 97% identity thereto.

6. The method of claim 1, wherein the at least one bacteriophage is formulated in a composition with a pharmaceutically acceptable excipient or carrier.

7. The method of claim 6, wherein the composition is a liquid, semi-liquid, solid or lyophilized formulation.

8. The method of claim 1, which comprises the administration of between $10^{e4}$ and $10^{e12}$ PFU of said at least one bacteriophage.

9. The method of claim 1, wherein the mammal is a human.

10. The method of claim 1, wherein the mammal has a bacterial infection.

* * * * *